Figure 1:
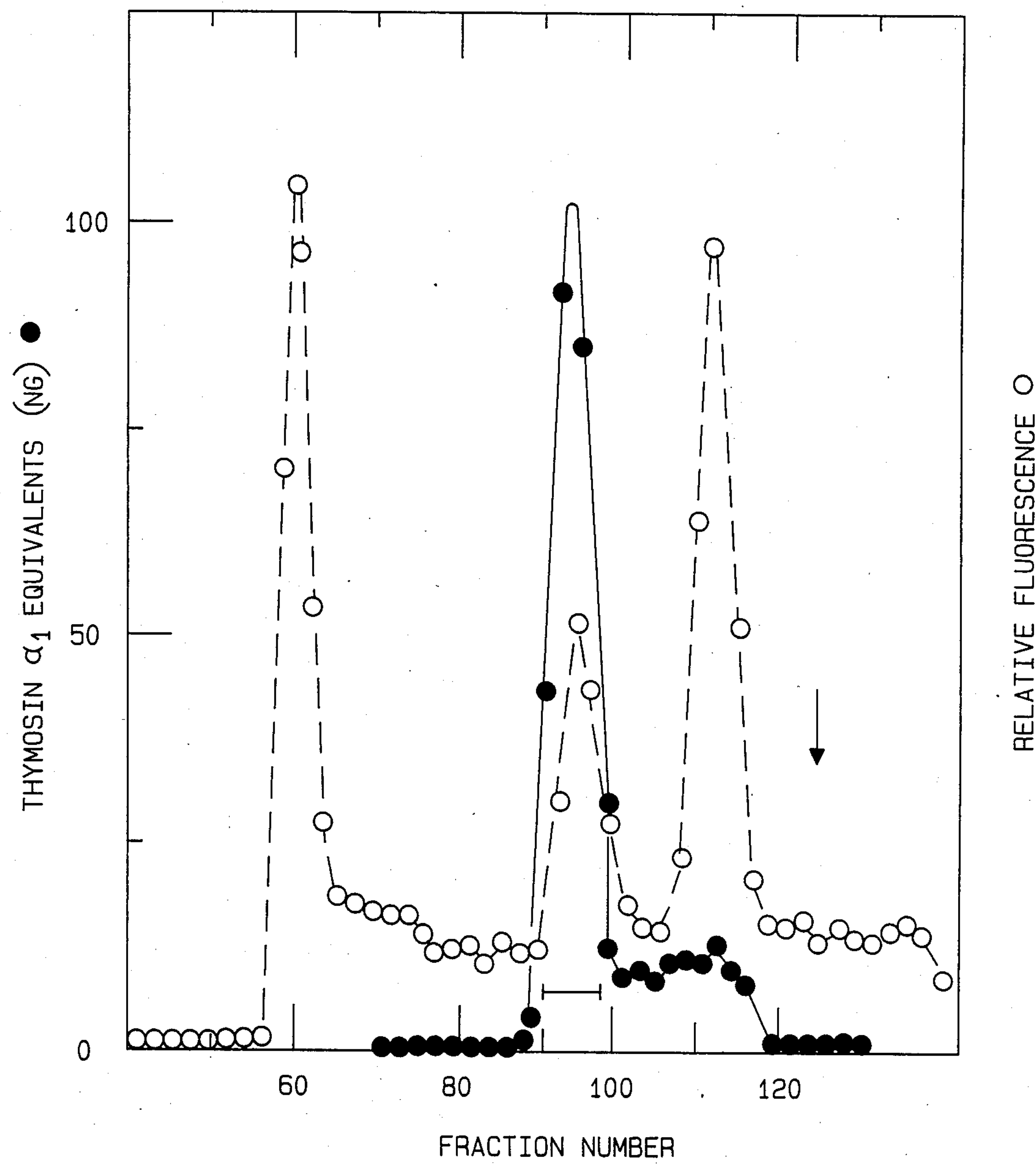

United States Patent [19]

Horecker

[11] Patent Number: 4,659,694

[45] Date of Patent: Apr. 21, 1987

[54] PROTHYMOSIN ALPHA

[75] Inventor: Bernard L. Horecker, New York, N.Y.

[73] Assignee: Hoffmann-La Roche Inc., Nutley, N.J.

[21] Appl. No.: 639,757

[22] Filed: Aug. 13, 1984

Related U.S. Application Data

[63] Continuation-in-part of Ser. No. 546,211, Oct. 27, 1983, abandoned.

[51] Int. Cl.[4] ........................ A61K 17/24; C07K 7/48; C07K 13/00

[52] U.S. Cl. ........................................ 514/12; 530/301; 530/350

[58] Field of Search ................. 260/112.5 R; 530/301, 530/350; 514/12

[56] References Cited

U.S. PATENT DOCUMENTS

| | | | |
|---|---|---|---|
| 3,657,417 | 4/1972 | Brunetti et al. | 424/95 |
| 4,010,148 | 3/1977 | Goldstein | 260/112.5 R |
| 4,082,737 | 4/1978 | McGregar et al. | 260/112.5 R |
| 4,239,498 | 11/1980 | Rule | 260/112.5 R |
| 4,250,084 | 2/1981 | Trainin | 260/112.5 R |
| 4,377,511 | 3/1983 | Lopukhin et al. | 260/112.5 R |

OTHER PUBLICATIONS

Haritos et al., *Proc. Natl. Acad. Sci.,* U.S.A., 81, 1008-1011 (1984).

Ritted et al., *Experientia,* 32(2), 246-248 (1976).

Rudinger, *Peptide Hormones,* Parsons (ed), U. Park Press, Baltimore 1-7 (1976).

*Primary Examiner*—Delbert R. Phillips

*Attorney, Agent, or Firm*—Jon S. Saxe; Bernard S. Leon; George M. Gould

[57] ABSTRACT

A new biological polypeptide hormone has been isolated from mammalian thymus and has been given the designation prothymosin alpha. This peptide contains approximately 107 to 113 amino acid residues depending on species and is distinguished by having the thymosin $alpha_1$ sequence at its amino-terminus. Prothymosin alpha appears to represent the native polypeptide from which thymosin $alpha_1$, thymosin $alpha_{11}$ and other fragments are generated during the isolation of thymosin fraction 5. Prothymosin alpha is one of several peptides isolated from thymic tissue which participate in the regulation, differentiation and function of thymic dependent lymphocytes (T cells). The new peptide appears to be more potent on a weight basis than thymosin $alpha_1$ in the protection of subject animals against opportunistic infections.

4 Claims, 8 Drawing Figures

THYMOSIN $\alpha_1$ EQUIVALENTS (NG) ●

RELATIVE FLUORESCENCE ○

100

50

0

60 80 100 120

FRACTION NUMBER

```
                      5                   10                  15
AcSer-Asp-Ala-Ala-Val-Asp-Thr-Ser-Ser-Glu-Ile-Thr-Thr-Lys-Asp-Leu-Lys-
         20                  25                  30
 Glu-Lys-Lys-Glu-Val-Val-Glu-Glu-Ala-Glu-Asn-Gly-Arg-
```

FIGURE 6

Figure 7:
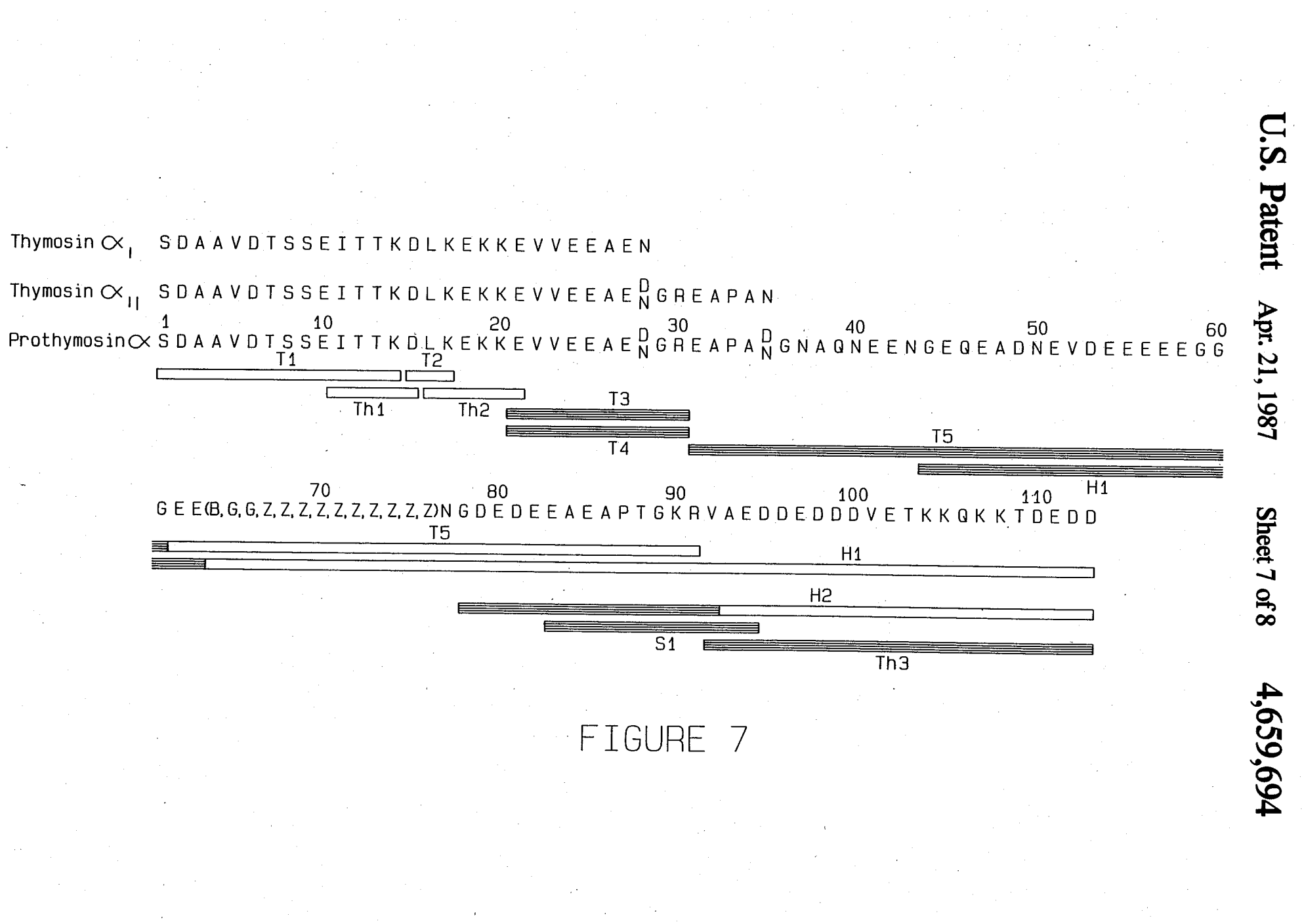

Thymosin α_I S D A A V D T S S E I T T K D L K E K K E V V E E A E N

Thymosin α_II S D A A V D T S S E I T T K D L K E K K E V V E E A E D/N G R E A P A N Prothymosin α (1, 10, 20, 30, 40, 50, 60) S D A A V D T S S E I T T K D L K E K K E V V E E A E D/N G R E A P A D/N G N A Q N E E N G E Q E A D N E V D E E E E E E G G T1 T2 Th1 Th2 T3 T4 T5 H1

PROTHYMOSIN ALPHA

RELATED APPLICATIONS

This is a continuation-in-part of copending application Ser. No. 546,211, filed Oct. 27, 1983, now abandoned.

BACKGROUND OF THE INVENTION

Thymosin fraction 5, known, for example, from U.S. Pat. No. 4,082,737, is a potent immunopotentiating preparation and can act in lieu of the thymus gland to reconstitute immune functions in thymic deprived and/or immunodeprived individuals. Ongoing clinical trials with fraction 5 suggest that thymosin is effective in increasing T cell numbers and normalizing immune functions in children with thymic dependent primary immunodeficiency disease and can increase T cell numbers in immunodepressed cancer patients.

The first active peptide isolated and characterized from thymosin fraction 5 has been termed thymosin $\alpha_1$. See, for example, U.S. Pat. No. 4,079,127 for a description of this peptide's isolation and characterization. Synthesis of thymosin $\alpha_1$ by solution and solid phase synthesis techniques is described in U.S. Pat. No. 4,148,788. Additionally, the synthesis of thymosin $\alpha_1$ by solution phase procedures is shown in U.S. Pat. No. 4,116,951. Thymosin $\alpha_1$ has been found to be one or more orders of magnitude more active than fraction 5 in several in vitro and in vivo assay systems designed to measure T cell differentiation and function. Thymosin $\alpha_1$ is currently in the clinic to determine its efficacy in the treatment of immunodeficiency diseases, immunodepressed cancer patients and in the prevention of opportunistic infections in immunosuppressed patients.

More recently, another related peptide designated thymosin $\alpha_{11}$ was shown to share the biological activities of thymosin $\alpha_1$. This peptide contained seven additional amino acid residues at the carboxy terminus when compared to thymosin $\alpha_1$. A description of its isolation and characterization is given in U.S. patent application Ser. No. 532,418, filed Sept. 15, 1983, now abandoned, inventor B. Horecker.

DESCRIPTION OF THE INVENTION

The present invention relates to the isolation and characterization of a new polypeptide isolated from mammalian thymus. This peptide has been termed prothymosin $\alpha$. Prothymosin $\alpha$ has been found to have the same approximate quantative and qualitative biological activity as has been observed for thymosin $\alpha_1$ in in vivo assay systems designed to measure T cell differentiations and function.

It has previously been known in the art that thymosin $\alpha_1$ is not detected in guanidiniun chloride extracts of calf thymus. This led to the suggestion that thymosin $\alpha_1$ might represent a proteolytic fragment of a larger native polypeptide which was supported by the further finding that preparations of calf thymosin fraction 5 contained at least two other related peptides. One of these, designated des-(25-28)-thymosin $\alpha_1$, contained only the first 24 amino acid residues; the other, named thymosin $\alpha_{11}$, contained the complete sequence of thymosin $\alpha_1$ plus seven additional residues at the carboxyl-terminus.

In an effort to isolate the native thymic polypeptide from which these fragments appear to be derived, a radioimmunoassay based on a antibody prepared against synthetic thymosin $\alpha_1$ was employed. In combination with this assay, a new procedure designed to eliminate any possibility of proteolytic modification was used to isolate a major polypeptide, approximately 107 to 113 amino acid residues long depending on species, that contains the thymosin alpha$_1$ sequence at its amino-terminus. This polypeptide has been designated prothymosin alpha because it appears to be the source of the thymosin $\alpha_1$-related peptide fragments found in preparations of thymosin fraction 5.

The method employed for the isolation of prothymosin from thymus tissue involved utilizing fresh frozen tissue which was pulverized under liquid nitrogen with a chilled mortar and pestle. The powdered frozen thymus was then quickly dispersed into boiling phosphate buffer, pH 7.0, and the boiling continued for a sufficient time to inactivate all proteases that might be present. This suspension was then worked up to yield the desired prothymosin $\alpha$.

The specific embodiments by which prothymosin $\alpha$ was isolated from rat and human thymus glands is set forth below.

Materials and Methods

Rat thymuses from male Charles River CD rats, 5 weeks old, were excised immediately following sacrifice of the animals by decapitation, quickly frozen in liquid nitrogen and stored at $-70°$ C. Synthetic thymosin $\alpha_1$ was generously provided by Dr. A. Felix of Hoffmann-La Roche Inc. Trypsin (TPCK-treated) and Staphylococcus V8 Protease were from Worthington and Miles Laboratories respectively. Fluorescamine was a gift of Dr. W. E. Scott of Hoffmann-La Roche Inc. Sephacryl S-200 (Superfine) was purchased from Pharmacia. Other reagents and solvents were chromatography-grade commercial preparations, the solvents were redistilled as required.

A synthetic thymosin $\alpha_1$-keyhole limpet hemocyanin (KLH) conjugate was synthesized by glutaraldehyde cross-linking. 2 mg of synthetic thymosin $\alpha_1$ were dissolved in 1 ml of KLH solution brought to absorbance 2.0 at 280 nm by dialysis against phosphate buffered saline (PBS) and dilution with the same buffer. To this solution 8 aliquots of 3 $\mu$l each of glutaraldehyde 25% were added while vortexing (final concentration of glutaraldehyde 0.6% (v/v)). The reaction was left for completion for 3 hours at room temperature with mild agitation. Subsequently, the incubation mixture was dialysed against PBS at 4° C. The dialysed product was mixed with an equal volume of Freund's adjuvant and was injected in male New Zealand white rabbits. They received primary immunization by multiple (30–40) intradermal injection, with 1 mg of conjugate in Freund's complete adjuvant. The animals were boosted five weeks later via the same route with 0.8 mg conjugate in Freund's incomplete adjuvant. Further booster injections were given according to the latter protocol as dictated by a decline of antibody titre. Animals were bled routinely from the ear vein, the blood allowed to clot and the supernatant solution was used as the antiserum. For the radioimmune assay a derivative of thymosin $\alpha_1$ labeled with tritium by reaction of the lysyl residues with formaldehyde and reduction of the N-methylene groups with sodium borotritiide (Amersham Corp., 8.5 Ci/mmol) was prepared.

The quantitative radioimmune assay was standardized with unlabeled synthetic thymosin $\alpha_1$ and the results expressed as thymosin $\alpha_1$ equivalents. The method was capable of detecting as little as 2 pmol of thymosin $\alpha_1$ and yielded consistently reproducible results in the range from 3 to 40 pmol of thymosin $\alpha_1$.

Details of procedures for gel filtration, HPLC and isoelectric focusing are described in the text. The HPLC experiments were carried out with an Altex Ultrasphere ODS C18 column using an apparatus equipped with Waters Associates Model 720 Systems Controller and Model 710B Intelligent Sample Processor, adapted for fluorescence detection after derivitization with fluorescamine. See Stein and Moschera, *Methods In Enzymology* 79, 7(1981). Protein was determined by the method of Lai, *Methods In Enzymology* 47, 236(1977).

Results

Isolation of prothymosin α.

To prevent the formation of smaller immunoreactive peptides it was found necessary to inactivate proteolytic enzymes before the frozen tissue was allowed to thaw. In the method finally selected, the frozen tissue was pulverized under liquid nitrogen with a chilled mortar and pestle. Batches of powdered frozen thymus (7 g each) were quickly dispersed into 100 ml portions of boiling 0.1M Na phosphate buffer, pH 7.0, and boiling continued for 5 minutes. The suspensions were then cooled in ice. Four such suspensions were combined and homogenized with three 30-second bursts at top speed with a Polytron homogenizer (Brinkman Type P710/35). The resulting homogenate was centrifuged for 30 minutes at 12,000 xg. Subsequent operations were carried out at room temperature. The clear supernatant solution (347 ml) was diluted with an equal volume of buffer A (1M HCOOH/0.2M pyridine, pH 2.8) and forced through banks of three Sep-Pak C18 cartridges (Waters Associates) mounted in series. For the extract derived from 28 g of tissue, 28 such sets of three cartridges (84 total) were required. The cartridges containing the adsorbed peptides were washed with buffer A (20 ml for each set of 3 cartridges) and each set was eluted with 10 ml of the same buffer containing 20% 1-propanol. The recovery of immunoreactive material in the combined eluates was 63% of that present in the solution applied to the Sep-Paks.

The combined Sep-Pak eluates were lyophilized and the viscous residues dissolved in 2.4 ml of buffer A (final volume=3.2 ml). Aliquots (0.8 ml), containing peptides recovered from 7 g of thymus tissue, were chromatographed on a column of Sephacryl S-200 (FIG. 1). The immunoreactive peptide(s) emerged in a single sharp peak with an elution position corresponding to a molecular weight of approximately 32,000.

Figure 2:
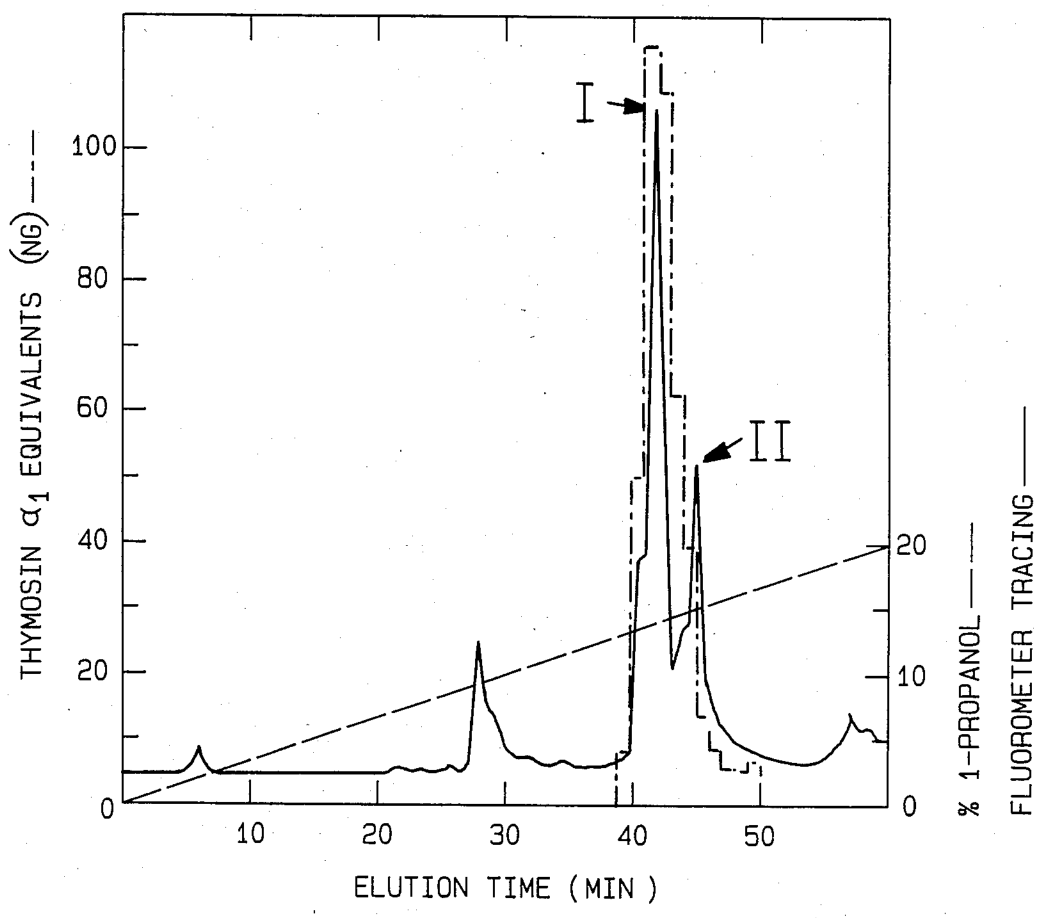

The peptides recovered from the Sephacryl S-200 column were separated and purified by HPLC (FIG. 2). A major peptide peak (peak I) containing the bulk of the immunoreactivity was followed by a smaller peak (peak II) containing a second peptide that appeared to be weakly immunoreactive. From 28 g of rat thymus after HPLC, there was recovered 1.6 mg of peptide in peak I based on amino acid analysis of an aliquot hydrolyzed in 5.7N HCl.

Rechromatography of an aliquot of the peptide recovered in peak I yielded a sharp peak, with an elution time of 42–43 minutes, slightly later than the elution time of thymosin $\alpha_1$, which emerged almost precisely at 41 minutes under the conditions employed (FIGS. 3A, B). When a mixture of the two peptides was analyzed, each emerged at the expected position and the two were clearly separated (FIG. 3C). The new immunoreactive peptide was named prothymosin α.

Figure 4:
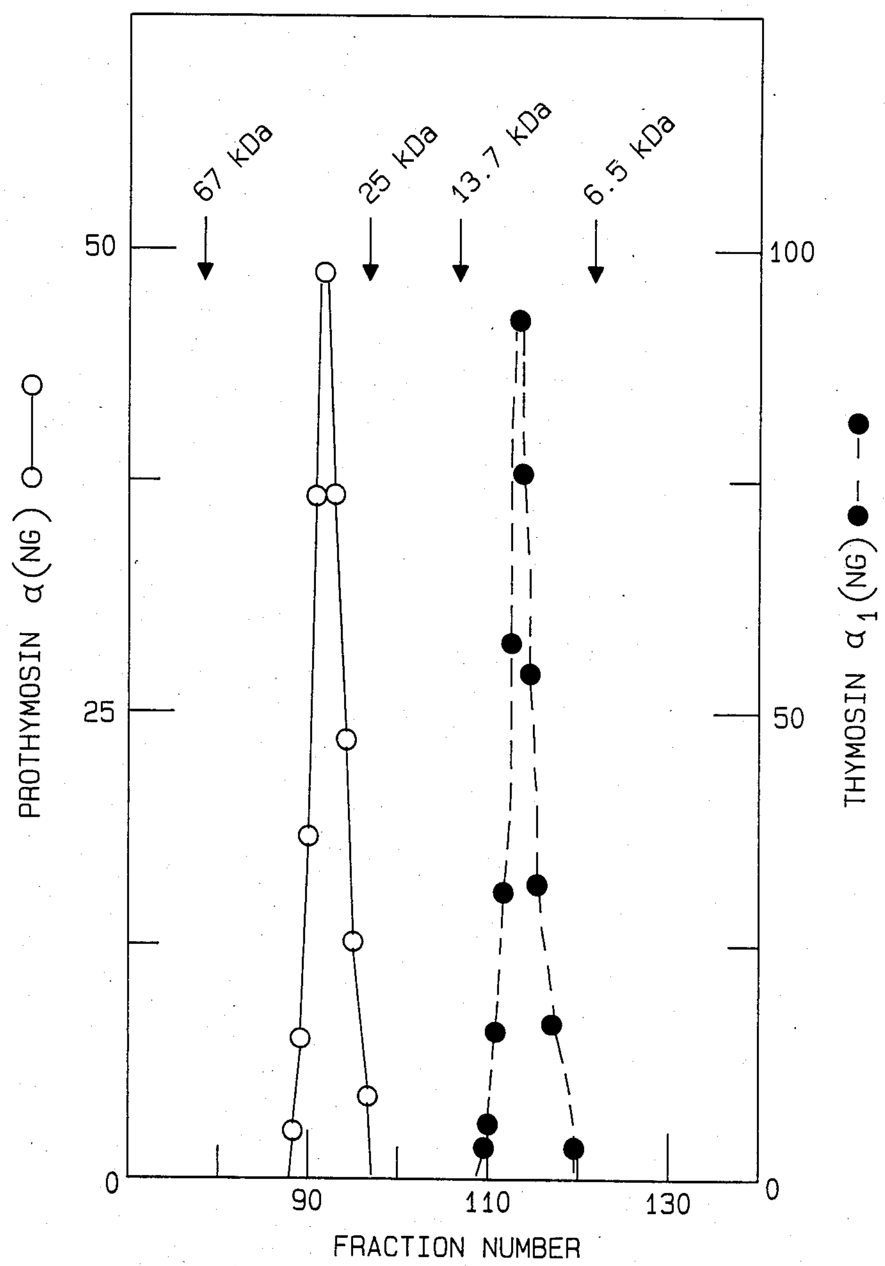

The elution pattern of the major immunoreactive peptide on HPLC was consistent with that of a small peptide resembling thymosin $\alpha_1$. On the other hand, its behavior on the Sephacryl S-200 column suggested a molecular weight in excess of 30,000, or alternatively, binding of the peptide to a larger polypeptide carrier. In order to distinguish between these alternatives, the peptide recovered from the HPLC column in peak I was rechromatographed on the same Sephacryl S-200 column (FIG. 4). The purified peptide emerged as a single sharp peak with the same elution volume as before. On the same column a sample of synthetic thymosin $\alpha_1$ emerged somewhat later, at a position corresponding to an apparent molecular weight of approximately 11,000. As discussed later, both peptides show a tendency to form oligomers.

Properties of prothymosin α.

Figure 5:
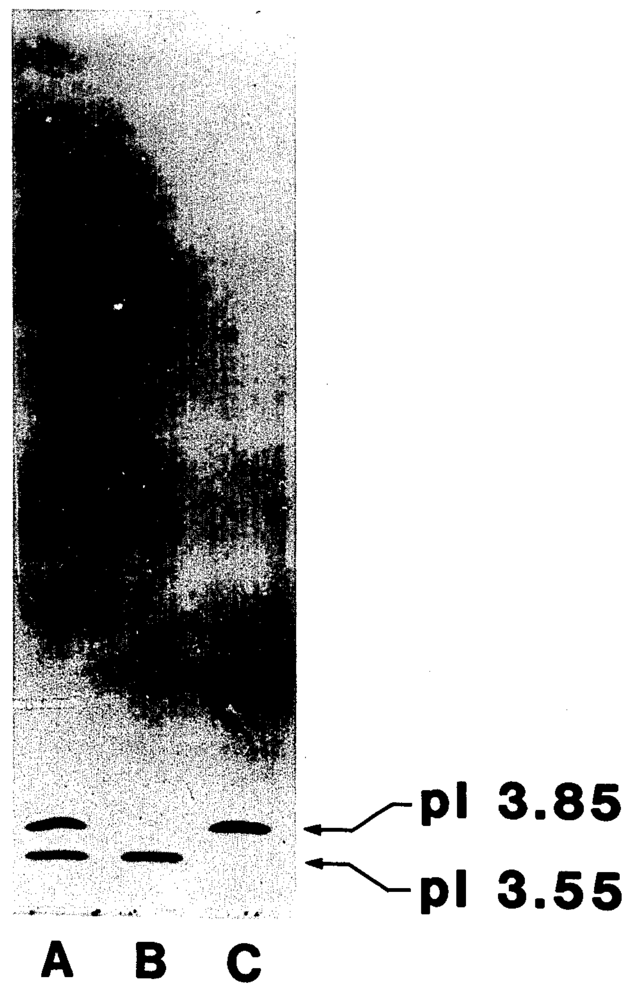

The purified prothymosin α preparations yielded a single band of analytical isoelectric focusing, with pI=3.55 (FIG. 5). On the same gels synthetic thymosin $\alpha_1$ focused at a position corresponding to pI=3.85.

Amino acid analysis (Table 1) showed prothymosin α to be unusually rich in glutamic and aspartic acids, which accounted for one-third and nearly one-fourth of the total amino acids, respectively. Cysteine, methionine, histidine and the aromatic amino acids were not detected. The minimum chain length, calculated assuming one residue each of leucine and isoleucine, for rat prothymosin alpha was approximately 113; the minimum molecular weight calculated from the amino acid composition was 12,600. This value was confirmed by the results of tryptic digestion which yielded only one peptide containing leucine and one containing isoleucine.

TABLE 1

Amino Acid Composition of rat prothymosin alpha

| | Prothymosin α | Thymosin $\alpha_1$ | Thymosin $\alpha_{11}$ |
|---|---|---|---|
| Asx | 25.6 ± 0.8 (26) | 4 | 5 |
| Thr | 6.0 ± 0.2 (6) | 3 | 3 |
| Ser | 3.2 ± 0.2 (3) | 3 | 3 |
| Glx | 39.6 ± 2.7 (40) | 6 | 7 |
| Gly | 5.3 ± 0.3 (5) | 0 | 1 |
| Ala | 10.3 ± 0.7 (10) | 3 | 5 |
| Val | 5.9 ± 0.2 (6) | 3 | 3 |
| Ile | 1.0 ± 0.0 (1) | 1 | 1 |
| Leu | 1.0 ± 0.1 (1) | 1 | 1 |
| Lys | 9.8 ± 0.3 (10) | 4 | 4 |
| Arg | 2.3 ± 0.2 (2) | 0 | 1 |
| Pro | 2.4 ± 0.6 (2) | 0 | 1 |
| Total | (112) | 28 | 35 |

The values shown are the means and standard deviations from analyses of four samples of prothymosin α hydrolysed with redistilled 5.7M HCl at 150° C. for 1 hour, and analyzed with a Glenco MM-70 amino acid analyzer adapted for use of o-phthaldehyde and fluorescence detection as described by Benson and Hare, *Proc. Natl. Acad. Sci. U.S.A.* 72, 619(1975). Proline was analyzed in an apparatus providing for oxidation of proline with N-chlorosuccinimide as described by Weigle et al., *Biochem. Biophys. Res. Commun,* 50, 352(1973). The values are calculated assuming a value of 1.0 for isoleucine. The nearest integral numbers are shown in parentheses. Tryptophan detection was carried out according to Simpson et al., *Proc. Natl. Acad, Sci U.S.A.* 251,1936 (1976). Cysteine detection was carried out according to Hirs, *Methods In Enzymology* 11, 59(1967). Neither of these residues was present in prothymosin α.

The amino terminus of prothymosin α was found to be blocked, supporting the conclusion that this part of the molecule carries the immunoreactive thymosin $\alpha_1$ sequence. Tryptic digests of prothymosin α yielded peptides whose elution position in HPLC and amino acid compositions indicated identity with peptides 1–14 (containing the single isoleucine residue), 15–17 (containing the single leucine residue), and 18–20 of thymosin $\alpha_1$ (FIG. 6) and also with peptide 21–30 (containing the single arginine residue) of thymosin $\alpha_{11}$. The tryptic peptide corresponding to residues 1–14 was also detected with the anti-thymosin $\alpha_1$ antibody. Digestion with *Staphylococcus aureus* V8 Protease, which hydrolyzes glutamyl bonds, yielded a blocked peptide that could be detected with fluorescamine but was immunoreactive. The amino acid composition of this peptide ($Ser_3$, $Asp_2$, $Ala_2$, Val, Thr, Glu) confirmed that it corresponded to the blocked $NH_2$-terminal decapeptide of thymosin $\alpha_1$. No carbohydrate was detected by HPLC analysis of acid hydrolysates of prothymosin α.

The biological activity of prothymosin α can be determined by utilizing in vivo assays known in the art. Thus, for example, inbred strains of mice are known to vary in their susceptability to infection with *C. albicans.* Thus, mice of such strains as $C_3H$/HeJ or AKR/J are highly susceptible to infection, whereas mice of such strains as $C_{57}$ B1/10SNJ or $C_{57}$B1/KsJ were highly resistant to challenge. Since resistance to infection with *C. albicans* is associated with cell-mediated processes, and therefore with T-lymphocytes, thymic hormones should have an effect on the host response. Thymosin fraction 5 and some peptides derived therefrom have been found to enhance maturation and replication of T-lymphocytes (Goldstein et al., Rec. Progress in Hormone Research 37, 369–415(1981)) and accordingly should influence the resistance of a susceptible murine strain, such as $C_3H$/HeJ, to infection with *C. albicans.*

Prothymosin α was injected daily i.p. in graded doses into different groups of mice, beginning two days before intravenous challenge with $4\times10^4$ cells of *C. albicans.* In comparison with control mice, prothymosin α provided protection and most notably at a dose of 160 ng/mouse provided complete elimination of infecting organisms, a result not achieved with other thymic peptides including thymosin $\alpha_1$ and thymosin $\alpha_{11}$. The results are summarized in Table 2 below.

TABLE 2

Effect of Prothymosin α on the Growth of *Candida Albicans* in Kidneys of $C_3H$/HeJ and AKR/J Mice

| Dose | *C. albicans* cell counts in left kidneys | |
|---|---|---|
| ng/mouse | $C_3H$/HeJ mice | AKR/J mice |
| 0 | 10,000 (2) | 10,000 (50% died) (4) |
| 80 | 66–72 (4) | 0–520 (2) |
| 160 | 0 (4) | 0 (4) |
| 320 | 0 (4) | 280–480 (3) |
| 640 | 10,000 (4) | not done |

Mice (number of animals for each dose given in parens) were treated daily with the indicated doses of prothymosin and challenged with $4\times10^4$ cells of *C. albicans* two days after the start of treatment. They were sacrificed on day 14 and the number of organisms in the left kidneys determined by grinding the tissue in sterile sand and plating dilutions of the suspensions on Sabouroud's agar. Colonies were counted after incubation of the plates for 72 hours at 37° C.

Prothymosin α, in analogy to thymosin $\alpha_1$, may be administered to warm-blooded mammals by parenteral application either intravenously, subcutaneously or intramuscularly. The compound is a potent immunopotentiating agent with a daily dosage in the range of about 1–100 microgram/kg of body weight per day, for intravenous administration. Obviously, the required dosage will vary with the particular condition being treated, the severity of the condition and the duration of the treatment. A suitable dosage form for pharmaceutical use is 1 mg of lyopholized prothymosin α per vial to be reconstituted prior to use by the addition of sterile water or saline.

Also included within the scope of the present invention are the pharmaceutically acceptable salts of prothymosin α such as the sodium or potassium salts or salts with strong organic bases such as guanidine. In addition, the counterions of these cations as well as lysine residues in prothymosin α, such as the hydrochloride, hydrobromide, sulfate, phosphate, maleate, acetate, citrate, benzoate, succinate, ascorbate and the like, may be included in the preparation.

It is also within the scope of the present invention to modify the sequence of prothymosin α by single amino acid changes or by derivatizing the carboxyterminus by ester or amide formation. Also, within the scope of the invention is the unblocked aminoterminus analog desacetylprothymosin α which can be produced directly by the use of recombinant DNA techniques by employing a gene derived by isolation of the natural prothymosin α gene utilizing nucleotide probes derived from the known sequence of the aminoterminus of the peptide. The desacetylprothymosin can be converted to prothymosin α using selective $NH_2$-terminal acetylation by procedures known in the art for the conversion of desacetyl thymosin $\alpha_1$ to thymosin $\alpha_1$.

Discussion

Prothymosin α appears to be the native polypeptide from which the smaller fragments containing the thymosin $\alpha_1$ sequence, including thymosin $\alpha_1$ itself, are probably generated during the isolation of the preparation called thymosin fraction 5. The amino-terminal sequence of prothymosin α appears to be identical to that of thymosin $\alpha_1$; the COOH-terminal extension, approximately 85 amino acid residues long, is rich in acidic amino acids, accounting for the low isoelectric point, pH = 3.55, (FIG. 5) which is even lower than the value of 3.85 found for thymosin $\alpha_1$.

Both prothymosin α and thymosin $\alpha_1$ appear to form oligomers in aqueous solution. In gel filtration at pH 2.8, both of these peptide behave as discrete oligomers, possibly trimers. In similar gel filtration experiments carried out at pH 7.0, they emerge as sharp peaks corresponding to molecular weights of 61,000 for prothymosin and 15,000 for thymosin $\alpha_1$ possibly corresponding to hexamers. Intermediate forms were not detected. Binding to a larger carrier polypeptide in the gel filtration experiment is excluded by the identical behavior of prothymosin after purification by HPLC. This tendency to oligomerize may be a consequence of the amphoteric nature of these peptides.

Prothymosin α is observed to be readily converted to smaller fragments unless special precautions are taken to inactivate proteinases before or during extraction of the tissue. The formation of these fragments may be related to its biological activity. Both thymosin $\alpha_1$ and thymosin $\alpha_{11}$ have been shown to protect sensitive strains of mice against opportunistic infections. Initial tests indicate that prothymosin is also active in these assays at doses smaller than those required with thymosin $\alpha_1$ or thymosin $\alpha_{11}$. This indicates that the activity is due to prothymosin $\alpha$ and not to its conversion in vivo to thymosin $\alpha_1$ and/or thymosin $\alpha_{11}$.

The amino acid composition and low isoelectric point of prothymosin $\alpha$ suggests an unusual acidic structure.

Partial Sequence of Rat Prothymosin Alpha

Materials

All chemicals and solvents employed were chromatography grade. Trypsin (TPCK-treated) was purchased from Worthington Biochemical Corporation, *Staphylococcus aureus* V8 protease from Miles Laboratories Inc., thermolysin and carboxypeptidase Y from Sigma Chemical Company. Hydroxyalamine was from Mallinckrodt Chemical Works. Prothymosin alpha was isolated from rat thymus as discussed above.

Methods

*S. aureus* V8 protease digestion was carried out by adding 1.9 μg of the enzyme to 75 μg of prothymosin alpha dissolved in 54 ul of 50 mM ammonium acetate solution pH 4.0. After incubation for 15 h at room temperature the sample was lyophylized, dissolved in buffer A (1M formic acid and 0.2M pyridine) and the peptide fragments separated on HPLC.

Digestion with thermolysin was made by adding 10 μg of the enzyme to 267 μg of prothymosin alpha dissolved in 25 μl of 0.12M ammonium bicarbonate solution. After incubation for 2 h at 37° C., the sample was lyophylized, dissolved in buffer A and run on HPLC.

Trypsin digestion was carried out by adding 10 ug of TPCK-trypsin dissolved in 1 mM hydrochloric acid to 200 μg of prothymosin alpha dissolved in 52 μl of 0.4M pyridine. After incubation for 15 h at room temperature, the reaction was terminated by the addition of 0.4 μl of formic acid. To this solution 60 μl of buffer A were added and the sample was fractionated by HPLC.

For the hydroxylamine hydrolysis 400 μg of prothymosin alpha were dissolved in 60 μl of 2M hydroxylamine solution adjusted to pH 9.0 by potassium bicarbonate. After incubation for 14 h at 50° C. the reaction was terminated by the addition of 26 μl of formic acid and 64 μl of buffer A, and the sample run on HPLC.

For the carboxypeptidase Y digestion 20 μg of prothymosin alpha were dissolved in 96 μl of 50 mM NaAcetate buffer, pH 5.0. To this, 10 μg of carboxypeptidase Y were added. At timed intervals 5–10% of the total volume was removed, and diluted to 100 μl with ice cold buffer containing 67 mM $Na_2$-citrate, pH 2.0, containing 1.5% n-propanol (v/v) and norleucine as internal standard, and frozen for subsequent amino acid analysis.

The peptides generated by enzymatic digestion and chemical hydrolysis were isolated by reverse phase HPLC. An Altex Ultrasphere ODS C18 column (5 μm, 0.46 cm×25 cm) was used. The column was equilibrated with buffer A and after the injection of the sample, was washed with buffer A for 20 min and the bound peptides eluted with a 120 min gradient of 0–40% acetonitrile in buffer A. The flow rate was 0.6 ml/min and 1 min fractions were collected.

The amino acid analysis were carried out as described above.

For the amino acid sequence analysis automated Edman degradations of peptides (0.5–1.5 nmol) were performed on a gas-phase sequenator (Applied Biosystems, Model 470A) according to Hewick et al. *J. Biol. Chem*, 256, 7990(1981) Phenylthiohydantoin derivatives of amino acids were separated on HPLC by using an Ultrasphere ODS column (Altex) as described by Hawke et al. *Anal. Biochem* 120, 302(1982).

Results

The strategy used to determine the sequence of rat prothymosin alpha was to obtain large overlapping peptides from specific chemical and enzymatic cleavages of the polypeptide. The primary structure proposed for prothymosin alpha (FIG. 7) represents a compilation of sequence data collected on peptides generated by trypsin (T), *S. aureus* V8 protease (S) and thermolysin (Th) and by chemical cleavages with hydroxylamine (H) specific for the asparaginyl-glycine bonds.

The amino terminus of prothymosin alpha could not be sequenced directly by automatic sequencing methods, using either prothymosin alpha or the amino-terminal peptide T1, suggesting that the amino terminus is blocked. The sequence of the first 20 amino acid residues of rat prothymosin alpha was assumed to be identical to that of calf thymosin alpha$_{11}$, the assumption based on the correct amino acid compositions of the fragments T1, T2, Th1 and Th2 (Table 3).

TABLE 3

| | Amino Acid Compositions of the Peptides shown in FIG. 7. | | | | | | | | | | |
|---|---|---|---|---|---|---|---|---|---|---|---|
| | (1–14) T1 | (15–17) T2 | (21–30) T3 | (21–30) T4 | (31–90) T5 | (11–15) Th1 | (16–21) Th2 | (92–113) Th3 | (44–113) H1 | (77–113) H2 | (83–94) S1 |
| * | | | | | | | | | | | |
| Asx | 2.0 | 1.0 | 1.3 | 1.0 | 10.1 | 1.1 | | 8.1 | 15.7 | 10.5 | 0.9 |
| Thr | 2.9 | | | | 1.4 | 1.9 | | 2.2 | 2.7 | 3.4 | 0.9 |
| Ser | 2.8 | | | | | | | | | | |
| Glx | 1.0 | | 4.0 | 4.0 | 23.4 | | 2.1 | 4.7 | 32.1 | 10.8 | 3.5 |
| Gly | | | 1.0 | 1.0 | 6.9 | | | | 7.3 | 3.0 | 1.2 |
| Ala | 2.0 | | 1.0 | 1.0 | 5.6 | | | 0.9 | 4.6 | 3.0 | 2.7 |
| Val | 1.0 | | 1.5 | 1.5 | 1.0 | | | 2.0 | 3.0 | 2.3 | 1.0 |
| Ile | 0.9 | | | | | 1.0 | | | | | |
| Leu | | 1.0 | | | | | 1.0 | | | | |
| Lys | 1.1 | 1.0 | 0.3 | 0.2 | 1.0 | 1.4 | 3.3 | 4.0 | 4.7 | 4.9 | 1.2 |
| Arg | | | 0.9 | 1.0 | | | | | 1.4 | 1.1 | 1.0 |

*Proline was not determined

Moreover, T1 was assigned as the aminoterminal peptide of prothymosin alpha since it was the only tryptic peptide having its amino terminus blocked and cross-reacting with an antiserum recognizing the residue 1–10 epitope of thymosin alpha$_1$. The sequence 21–30 appeared as a double peak on HPLC (peptides T3 and T4)

with identical amino acid compositions. Sequence analysis showed that the two peptides differed at the amino acid residue 28 containing Asp in T3 and Asn in T4. The molar concentration of T4 was twice that of T3. The aminoterminal Asp of the peptide T5 was assigned to position 31 on the basis of a four amino acid residue (32–35) overlap of peptide T5 with the known sequence of thymosin $alpha_{11}$. At position 31 we found the only difference between calf thymus $alpha_{11}$ and the first 35 amino acids of rat prothymosin alpha, the Glu residue in calf thymosin $alpha_{11}$ replaced by Asp in rat prothymosin alpha. Position 35 of prothymosin alpha appeared as both Asn (62%) and Asp (38%). The hydroxylamine derived peptide H1 formed by cleavage of the $Asn^{43}$-$Gly^{44}$ bond, made possible the sequencing of two additional residues beyond peptide T5 ($Glu^{62}$ and $Glu^{63}$). The subsequent stretch of approximately 13 residues could not be sequenced unambiguously due to the lack of any specific nearby cleavage point and the uncertainty encountered by its poly-Glu nature. The composition of the unsequenced residue was deduced from the difference of the experimental composition of the rat prothymosin alpha and the calculated composition of the sequenced prothymosin alpha (Table 4). Therefore subsequent residue position numbers must be considered tentative. Position 77 was identified as Asn since it preceeds the hydroxylamine peptide H2 starting at position 78. The thermolytic peptide Th3 represent the carboxyterminal peptide of prothymosin alpha. The needed overlap for peptides H2 and Th3 was provided by the peptide S1. The last 5 amino acids of prothymosin alpha (residues 109–113) were confirmed by the release of amino acids by the carboxypeptidase Y digestion of the polypeptide.

TABLE 4

Amino acid compositions of rat prothymosin alpha and of the sequenced and unsequenced segments of the polypeptide.

| | Prothymosin | Sequenced segment | Unsequenced segment |
|---|---|---|---|
| Asx | 24.2 ± 1.1 (24) | (23) | (1) |
| Thr | 6.3 ± 0.3 (6) | (6) | (0) |
| Ser | 3.5 ± 0.3 (3) | (3) | (0) |
| Glx | 39.0 ± 1.8 (39) | (29) | (10) |
| Gly | 10.5 ± 0.3 (10) | (8) | (2) |
| Ala | 10.1 ± 0.1 (10) | (10) | (0) |
| Val | 5.6 ± 0.2 (6) | (6) | (0) |
| Ile | 1.0 ± 0.0 (1) | (1) | (0) |
| Leu | 1.1 ± 0.1 (1) | (1) | (0) |
| Lys | 8.9 ± 0.3 (9) | (9) | (0) |
| Arg | 2.1 ± 0.1 (2) | (2) | (0) |
| Pro | 2.3 ± 0.5 (2) | (2) | (0) |
| Total | (113) | (100) | (13) |

Prior amino acid composition values for rat prothymosin alpha for glycine were found to be too low because of an error in the standard (compare Table 2 to Table 4 above). The present values are in good agreement with the results of sequence analysis.

Because of the possibility of deamidation during the heat inactivation of endogenous proteases employed for the isolation of prothymosin alpha, the amide assignments have been considered to be tentative. For the same reason the double occupancy of positions 28 and 35 by Asp and Asn could not be related to genetic polymorphism with any degree of certainty. However this possibility cannot be excluded since more than one genotype could be present in the large number of thymuses used in each of the 28 gr batches processed.

The deduced sequence for rat prothymosin alpha is set forth below:

10
AcSer—Asp—Ala—Ala—Val—Asp—Thr—Ser—Ser—Glu—Ile—

20
—Thr—Thr—Lys—Asp—Leu—Lys—Glu—Lys—Lys—Glu—

30
—Val—Val—Glu—Glu—Ala—Glu—(Asp/Asn)—Gly—Arg—Asp—

40
—Ala—Pro—Ala—(Asp/Asn)—Gly—Asn—Ala—Gln—Asn—Glu—

50
—Glu—Asn—Gly—Glu—Gln—Glu—Ala—Asp—Asn—Glu—

60
—Val—Asp—Glu—Glu—Glu—Glu—Glu—Gly—Gly—Gly—

70
—Glu—Glu(Asx,Glx,Glx,Glx,Glx,Glx,Glx,Glx,Glx,Glx,Glx,Gly,

80
Gly)Asn—Gly—Asp—Glu—Asp—Glu—Glu—Ala—Glu—Ala—

90
—Pro—Thr—Gly—Lys—Arg—Val—Ala—Glu—Asp—Asp—

100
—Glu—Asp—Asp—Asp—Val—Glu—Thr—Lys—Lys—Gln—

110
—Lys—Lys—Thr—Asp—Glu—Asp—AspOH.

Partial Sequence of Human Prothymosin Alpha

In direct analogy to the methods described above, human prothymosin alpha was isolated from frozen human thymus glands, purified and sequenced. The partial sequence obtained and deduced from experimental amino acid composition. The estimated total number of amino acid residues in human prothymosin alpha is 107.

The composition of human prothymosin alpha is set out below in Table 5.

TABLE 5

HUMAN PROTHYMOSIN α

| | Composition from amino acid analysis | Composition from known sequence | Calculated composition of the unknown sequence |
|---|---|---|---|
| Asx | 25.2 ± 0.7 (25) | (25) | (0) |
| Thr | 5.4 ± 0.3 (5) | (5) | (0) |
| Ser | 4.4 ± 0.3 (4) | (3) | (1) |
| Glx | 32.9 ± 1.1 (33) | (24) | (9) |
| Gly | 10.4 ± 0.2 (10) | (7) | (3) |
| Ala | 11.9 ± 0.5 (12) | (10) | (2) |
| Val | 4.7 ± 0.2 (5) | (5) | (0) |
| Ile | 1.0 ± 0.0 (1) | (1) | (0) |
| Leu | 1.1 ± 0.0 (1) | (1) | (0) |
| Lys | 8.2 ± 0.1 (8) | (8) | (0) |
| Arg | 2.2 ± 0.0 (2) | (2) | (0) |
| Pro | 1.1 ± 0.1 (1) | (1) | (0) |
| Total | (107) | (92) | (15) |

The primary structure of human prothymosin alpha and rat prothymosin alpha are set forth below:

1 10 20
R: xSer—Asp—Ala—Ala—Val—Asp—Thr—Ser—Ser—Glu—Ile—Thr—Thr—Lys—Asp—Leu—Lys—Glu—Lys—Lys—

-continued

```
H: xSer—Asp—Ala—Ala—Val—Asp—Thr—Ser—Ser—Glu—Ile—Thr—Thr—Lys—Asp—Leu—Lys—Glu—Lys—Lys—

                                        Asp      30                         Asp                         40
R: Glu—Val—Val—Glu—Glu—Ala—Glu—   —Gly—Arg—Asp—Ala—Pro—Ala—   —Gly—Asn—Ala—Gln—Asn—
                                        Asn                                 Asn
                                        Asp                                 Asp
H: Glu—Val—Val—Glu—Glu—Ala—Glu—   —Gly—Arg—Asp—Ala—Pro—Ala—   —Gly—Asn—Ala - - - - - Asn—
                                        Asn                                 Asn

                                                   50                                                  60
R: Glu—Glu—Asn—Gly—Glu—Gln—Glu—Ala—Asp—Asn—Glu—Val—Asp—Glu—Glu—Glu—Glu—Glu—Gly—Gly—
H: Glu—Glu—Asn—Gly—Glu—Gln—Glu—Ala—Asp—Asn—Glu—Val—Asp—Glu—Glu—Glu—Glu—Glu—Gly—Gly—

                                         70                                 80
R: Gly—Glu—Glu(Asx,Gly,Gly,Glx,Glx,Glx,Glx,Glx,Glx,Glx,Glx,Glx,Glx)Asn—Gly—Asp—Glu—
H: ..............................................................Asn—Gly—Asp—Glu—

                                                   90                                                  100
R: Asp—Glu—Glu—Ala—Glu—Ala—Pro—Thr—Gly—Lys—Arg—Val—Ala—Glu—Asp—Asp—Glu—Asp—Asp—Asp—
H: Asp—Glu—Glu—Ala—Glu— X — X — X —Gly—Lys—Arg—Ala—Ala—Glu—Asp—Asp—Glu—Asp—Asp—Asp—

                                                   110
R: Val—Glu—Thr—Lys—Lys—Gln—Lys—Lys—Thr—Asp—Glu—Asp—AspOH
H: Val—Asp—Thr—Lys—Lys—Gln—Lys - - - - - Thr—Asp—Asp—Asp—AspOH
```

x: Blocked amino terminus

- - -: Deletion

...: Sequence unknown and shorter than the equivalent sequence of rat prothymosin $\alpha$.

—X—: Sequence unknown

Asn/Asp: Approximately equal amounts of Asn and Asp are present at these positions.

Figure 8:
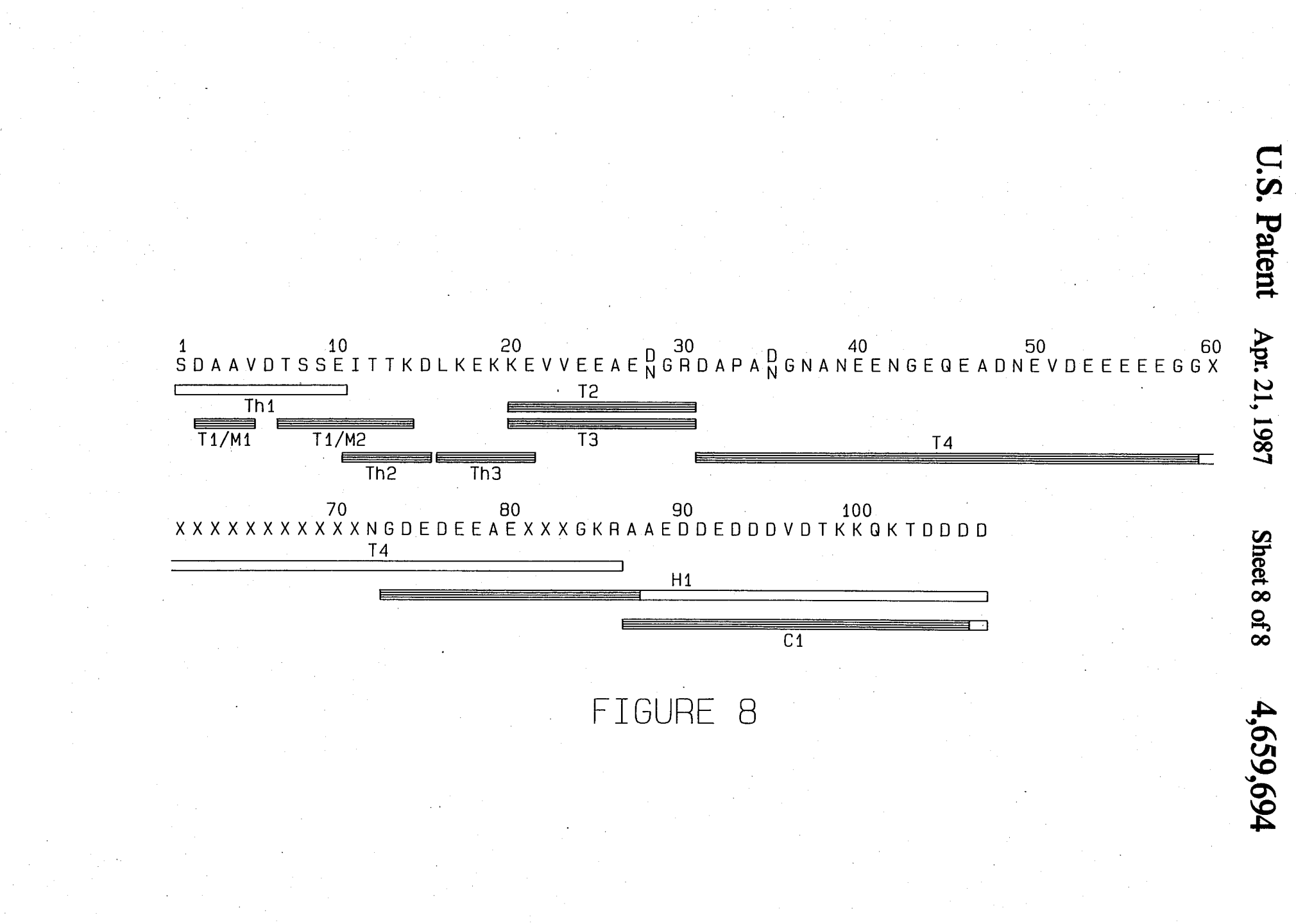

The schematic outline of the peptides used to establish the primary structure of human prothymosin alpha is shown in FIG. 8.

FIGURE LEGENDS

FIG. 1. Separation on Sephacryl S-200 of peptides extracted from boiled rat thymus tissue. Aliquots (0.8 ml) of the lyophylized material eluted from the Sep-Pak C18 cartridges, after solution in buffer A (see above), were applied to a column of Sephacryl S-200 (1.5 cm×89 cm), previously equilibrated with buffer A. The column was developed with the same buffer at a flow rate of 8.4 ml/h and 0.84 ml fractions were collected. for the radioimmunoassay, aliquots (7 $\mu$l) of each fraction were dried in a Speed Vac Concentrator (Savant). The assay mixture (500 $\mu$l) contained $10^4$ cpm of tritium-labeled thymosin $\alpha_1$, 20 $\mu$l of pre-immune serum and 5 $\mu$l of antiserum, sufficient to precipitate approximately 50% of the radioactivity, in 0.2M $NaPO_4$ buffer, pH 7.0. After 2 hours at room temperature, an equal volume of saturated $(NH_4)_2SO_4$ was added and 30 minutes later the solution was centrifuged and the pellet dissolved in 0.2 ml of 90% HCOOH, transferred to 10 ml of Aquasol (New England Nuclear) and the radioactivity determined. The assay was standardized with 0.5–500 ng of thymosin $\alpha_1$ and the results expressed as ng of thymosin $\alpha_1$ equivalents (solid line). To locate peptide peaks (dashed line) aliquots (10 $\mu$l) were dried, hydrolyzed with alkali and analyzed with fluorescamine as described by Lai (cited above). The elution position of synthetic thymosin $\alpha_1$ on the same column is illustrated by the arrow. For subsequent purification by HPLC, the fractions indicated by the bar were pooled and combined with similar fractions from three other gel-filtration separations.

FIG. 2. Separation of immunoreactive peptide(s) on reverse phase PHLC. The fractions comprising the immunoreactive peaks (pooled as described in the legend to FIG. 1) were lyophylized and the residue dissolved in 900 $\mu$l of buffer A. The HPLC experiments were carried out with 150 $\mu$l aliquots of this solution. Elution was with a gradient of 0–20% 1-propanol in buffer A as shown. Fractions (0.6 ml) were collected and 6 $\mu$l aliquots taken for radioimmune assay (see legend to FIG. 1). For analysis with fluorescamine, 5 $\mu$l aliquots were diverted every six seconds. In the preparation shown, fractions 42 and 43 (peak I) were pooled and combined with similar fractions from five other HPLC separations.

Figure 3:
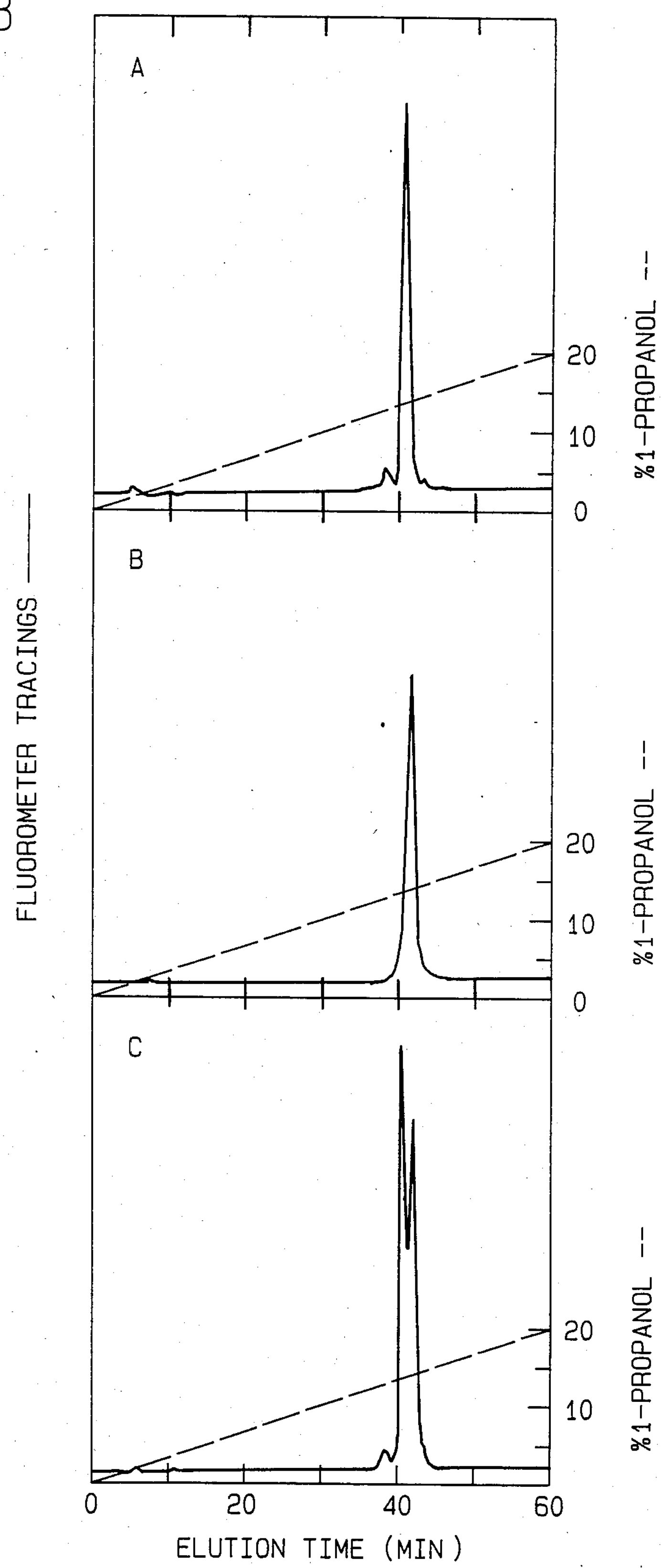

FIG. 3. Reverse phase HPLC of a mixture of purified rat prothymosin $\alpha$ and synthetic thymosin $\alpha_1$. The separations were carried out as described in the legend to FIG. 2 with 13.7 $\mu$g of synthetic thymosin $\alpha_1$ (A) or 35.2 $\mu$g of purified prothymosin $\alpha$ from peak I in FIG. 2 (B). A mixture of the two peptides analyzed on the same HPLC column yielded two peaks at the expected positions (C).

FIG. 4. Analysis on Sephacryl S-200 of purified rat prothymosin $\alpha$ and synthetic thymosin $\alpha_1$. Chromatography was carried out with the same column employed for the preparation described in FIG. 1. For prothymosin (solid line), 17.6 $\mu$g of purified peptide from peak I (see FIG. 2) was chromatographed at a flow rate of 8.8 ml/h and 0.88 ml fractions were collected. Aliquots (300 $\mu$l) were taken for radioimmune assay and the results are expressed as thymosin $\alpha_1$ equivalents. A sample of synthetic thymosin $\alpha_1$ (3.4 $\mu$g, dashed line) was chromatographed in the same way. Aliquots (100 $\mu$l) were taken for radioimmune assay. The results from the separate analyses were plotted together to show the relative elution position. For calculation of the apparent molecular weights, the same column was standardized with bovine serum albumin ($M_r$=67,000), chymotrypsinogen A ($M_r$=25,000), ribonuclease A ($M_r$=13,7000) and trypsin inhibitor ($M_r$=6,500).

FIG. 5. Analytical isoelectric focusing of rat prothymosin $\alpha$ and synthetic thymosin $\alpha_1$. Aliquots of prothymosin $\alpha$ (28 $\mu$g) and synthetic thymosin $\alpha_1$ (21 $\mu$g) were applied to one-half of an LKB Ampholine PAG plate (1804-102, pH range 4.0–6.5) and electrofocused for 2.5 hours with an LKB (Biochrome) 2103 Power Supply on a LKB (Bromma) 2117 Multiphor cooled to 10° C. For the one-half width plate the initial conditions were 200 V, 12.5 mA and the final conditions were 1500 V, 8.5 mA. The electrofocused slabs were fixed for 1 hour in 11.5% trichloracetic (w/v) acid and 3.45% sulfosalycilic acid (w/v). Staining was with 0.1% Coomassie brilliant blue solution (w/v) for 1 hour in 25% ethanol/8% acetic acid (v/v) followed by 0.1% Coomassie blue (w/v) in 25% 2-propanol/10% acetic acid (v/v) for 1 hour. Destaining was with 25% ethanol/8% acetic acid (v/v). A. Mixture of prothymosin α and thymosin $\alpha_1$. B. Prothymosin α. C. Thymosin $\alpha_1$.

FIG. 6. Amino-terminal sequence of rat prothymosin α. The sequence shown includes that reported for thymosin $\alpha_1$ (residues 1-28) and also for residues 1-30 thymosin $\alpha_{11}$. The peptides identified in tryptic digests of prothymosin α are indicated by the bars.

FIG. 7. The amino acid sequence of calf thymus thymosin alpha$_1$ and alpha$_{11}$ and rat thymus prothymosin alpha.

The schematic outline of the peptides used to establish the primary structure of prothymosin α is also shown. The peptides are designated according to the cleavage method used as follows: H, cleavage by hydroxylamine; S, *S. aureus* V8 protease; T, trypsin and Th, thermolysin. Full bars depict sequences established by automated Edman degradation. The amino terminus is blocked for all three peptides. In the case of thymosin $\alpha_1$ it is known to be acetylated. In parenthesis is the composition of the missing segment of prothymosin α based on the composition shown in Table 5. The sequence of the first 20 residues is based on the composition of the peptides $T_1$, $T_2$, $Th_1$ and $Th_2$ and the published sequences of thymosin $\alpha_1$ and thymosin $\alpha_{11}$. The COOH-terminal sequence DEDD was confirmed by the order of release of aspartic and glutamic acids by carboxypeptidase Y.

FIG. 8. The amino acid sequence of human prothymosin alpha. The peptides generated by digestion with thermolysin, trypsin and chlostripain are designated by the symbols Th, T and C, respectively. The peptides recovered after hydrolysis of peptide T1 with dilute acid is designated as T1/M1 and T1/M2. A peptide generated by cleavage with hydroxylamine is designated H1. Black bars show sequences established by automated sequence analysis. Open bars represent sequences based on amino acid compositions and homologies with overlapping peptides. Hydrolysis with dilute acide was carried out in sealed evacuated vials with 150 μl of 30 mM HCl at 110° C. for 15 h. Other digestions were as described in the text. Undetermined sequences are indicated by —X—. The composition of the unknown segment is $Ser_1$, $Glx_9$, $Gly_3$, $Ala_2$.

The one letter symbols represent: A, alanine; R, arginine; N, asparagine; D, aspartic acid; B, asparagine or aspartic acid; Q, glutamine; E, glutamic acid; Z, glutamine or glutamic acid; G, glycine; I, isoleucine; K, lysine; P, proline; S, serine; T, threonine; V, valine.

I claim:

1. A substantially homogeneous peptide and the pharmaceutically acceptable acid and base addition salts thereof, wherein said peptide comprises about 113 amino acid residues; wherein the isoelectric focusing point of said peptide is about 3.55; wherein about one half of the amino acid residues in said peptide consist of glutamic acid and aspartic acid; wherein said peptide does not contain methionine, cysteine or aromatic amino acids; wherein said peptide has the amino acid sequence starting from the amino terminal end:

1 10
Ser—Asp—Ala—Ala—Val—Asp—Thr—Ser—Ser—Glu—Ile—

20
—Thr—Thr—Lys—Asp—Leu—Lys—Glu—Lys—Lys—Glu—

30
—Val—Val—Glu—Glu—Ala—Glu—Asn—Gly—Arg—Asp—

40
—Ala—Pro—Ala—Asn—Gly—Asn—Ala—Glu—Asn—Glu—

50
—Glu—Asn—Gly—Glu—Gln—Glu—Ala—Asp—Asn—Glu—

60
—Val—Asp—Glu—Glu—Glu—Glu—Glu—Gly—Gly—Gly—

70
—Glu—Glu—Asx—Gly—Gly—Glx—Glx—Glx—Glx—Glx—

80
—Glx—Glx—Glx—Glx—Glx—Asn—Gly—Asp—Glu—Asp—

90
—Glu—Glu—Ala—Glu—Ala—Pro—Thr—Gly—Lys—Arg—

100
—Val—Ala—Glu—Asp—Asp—Glu—Asp—Asp—Asp—Val—

110
—Glu—Thr—Lys—Lys—Gln—Lys—Lys—Thr—Asp—

—Glu—Asp—Asp—

2. A substantially homogeneous peptide and the pharmaceutically acceptable acid and base addition salts thereof, wherein said peptide comprises about 109 amino acid residues; wherein the isoelectric focusing point of said peptide is about 3.55; wherein about one half of the amino acid residues in said peptide consist of glutamic acid and aspartic acid; wherein said peptide has the partial amino acid sequence starting from the amino terminal end:

10
Ser—Asp—Ala—Ala—Val—Asp—Thr—Ser—Ser—Glu—Ile—

20
—Thr—Thr—Lys—Asp—Leu—Lys—Glu—Lys—Lys—Glu—

30
—Val—Val—Glu—Glu—Ala—Glu—Asn—Gly—Arg—Asp—

40
—Ala—Pro—Ala—Asn—Gly—Asn—Ala—Asn—Glu—Glu—

50
—Asn—Gly—Glu—Gln—Glu—Ala—Asp—Asn—Glu—Val—

60
—Asp—Glu—Glu—Glu—Glu—Glu—Gly—Gly—Glu—Glu—

70
—Glu—Glu—Glu—Glu—Glu—Glu—Gly—Asp—Gly—Glu—

80
—Glu—Glu—Asp—Gly—Asp—Glu—Asp—Glu—Glu—Ala—

90
—Glu—Ser—Ala—Thr—Gly—Lys—Arg—Ala—Ala—Glu—

100
—Asp—Asp—Glu—Asp—Asp—Asp—Val—Asp—Thr—Lys—

109
—Lys—Gln—Lys—Thr—Asp—Glu—Asp—Asp—

3. A pharmaceutical dosage form for parenteral administration comprising a pharmaceutically acceptable parenteral carrier material and as the active agent a substantially homogeneous peptide, and the pharmaceutically acceptable acid and base addition salts thereof, wherein said peptide comprises about 109 amino acid residues; wherein the isoelectric focusing point of said peptide is about 3.55; wherein about one half of the amino acid residues in said peptide consist of glutamic acid and aspartic acid; wherein said peptide has the amino acid sequence starting from the amino terminal end:

10
Ser—Asp—Ala—Ala—Val—Asp—Thr—Ser—Ser—Glu—Ile—
20
—Thr—Thr—Lys—Asp—Leu—Lys—Glu—Lys—Lys—Glu—
30
—Val—Val—Glu—Glu—Ala—Glu—Asn—Gly—Arg—Asp—
40
—Ala—Pro—Ala—Asn—Gly—Asn—Ala—Asn—Glu—Glu—
50
—Asn—Gly—Glu—Gln—Glu—Ala—Asp—Asn—Glu—Val—
60
—Asp—Glu—Glu—Glu—Glu—Glu—Gly—Gly—Glu—
70
—Gly—Glu—Glu—Glu—Glu—Glu—Glu—Gly—Asp—Gly—Glu—
80
—Glu—Glu—Asp—Gly—Asp—Glu—Asp—Glu—Glu—Ala—
90
—Glu—Ser—Ala—Thr—Gly—Lys—Arg—Ala—Ala—Glu—
100
—Asp—Asp—Gln—Asp—Asp—Asp—Val—Asp—Thr—Lys—
109
—Lys—Gln—Lys—Thr—Asp—Glu—Asp—Asp—

4. A pharmaceutical dosage form for parenteral administration comprising a pharmaceutically acceptable parenteral carrier material and as the active agent a substantially homogeneous peptide, and the pharmaceutically acceptable acid and base addition salts thereof, wherein said peptide comprises about 113 amino acid residues; wherein the isoelectric focusing point of said peptide is about 3.55; wherein about one half of the amino acid residues in said peptide consist of glutamic acid and aspartic acid; wherein said peptide has the partial amino acid sequence starting from the amino terminal end:

1 10
Ser—Asp—Ala—Ala—Val—Asp—Thr—Ser—Ser—Glu—Ile—
20
—Thr—Thr—Lys—Asp—Leu—Lys—Glu—Lys—Lys—Glu—
30
—Val—Val—Glu—Glu—Ala—Glu—Asn—Gly—Arg—Asp—
40
—Ala—Pro—Ala—Asn—Gly—Asn—Ala—Gln—Asn—Glu—
50
—Glu—Asn—Gly—Glu—Gln—Glu—Ala—Asp—Asn—Glu—
60
—Val—Asp—Glu—Glu—Glu—Glu—Glu—Gly—Gly—Gly—
70
—Glu—Glu—Asx—Gly—Gly—Glx—Glx—Glx—Glx—Glx—
80
—Glx—Glx—Glx—Glx—Glx—Asn—Gly—Asp—Glu—Asp—
90
—Glu—Glu—Ala—Glu—Ala—Pro—Thr—Gly—Lys—Arg—
100
—Val—Ala—Glu—Asp—Asp—Glu—Asp—Asp—Asp—Val—
110
—Glu—Thr—Lys—Lys—Gln—Lys—Lys—Thr—Asp—
—Glu—Asp—Asp—.

* * * * *

UNITED STATES PATENT AND TRADEMARK OFFICE
CERTIFICATE OF CORRECTION

PATENT NO. : 4,659,694

DATED : April 21, 1987

INVENTOR(S) : Horecker

It is certified that error appears in the above-identified patent and that said Letters Patent is hereby corrected as shown below:

On the last page, Column 15, Line 30, please delete "-Gly-" as the first amino acid and insert therefor -Glu-.

Signed and Sealed this

Twelfth Day of July, 1988

*Attest:*

DONALD J. QUIGG

*Attesting Officer* *Commissioner of Patents and Trademarks*